US010914688B2

(12) United States Patent
Ayub et al.

(10) Patent No.: US 10,914,688 B2
(45) Date of Patent: Feb. 9, 2021

(54) DETECTING SATURATION LEVELS OF A SAMPLE CORE USING ELECTROMAGNETIC WAVES

(71) Applicants: Saudi Arabian Oil Company, Dhahran (SA); King Abdullah University of Science and Technology, Thuwal (SA)

(72) Inventors: Muhammad Ayub, Dhahran (SA); Muhammad Arsalan, Dhahran (SA); Muhammad Akram Karimi, Thuwal (SA); Atif Shamim, Thuwal (SA)

(73) Assignees: Saudi Arabian Oil Company, Dhahran (SA); King Abdullah University of Science and Technology, Thuwal (SA)

( * ) Notice: Subject to any disclaimer, the term of this patent is extended or adjusted under 35 U.S.C. 154(b) by 267 days.

(21) Appl. No.: 15/907,575

(22) Filed: Feb. 28, 2018

(65) Prior Publication Data
US 2019/0265173 A1 Aug. 29, 2019

(51) Int. Cl.
| G01V 3/00 | (2006.01) |
| G01N 22/04 | (2006.01) |
| G01N 33/24 | (2006.01) |
| G01N 27/22 | (2006.01) |
| G01N 15/08 | (2006.01) |
| E21B 49/00 | (2006.01) |
| E21B 49/02 | (2006.01) |
| E21B 43/00 | (2006.01) |

(52) U.S. Cl.
CPC ............. *G01N 22/04* (2013.01); *G01N 15/08* (2013.01); *G01N 27/221* (2013.01); *G01N 33/24* (2013.01); *G01N 33/241* (2013.01); *E21B 43/00* (2013.01); *E21B 49/00* (2013.01); *E21B 49/005* (2013.01); *E21B 49/02* (2013.01)

(58) Field of Classification Search
CPC .... G01N 33/241; G01N 33/24; G01N 27/221; G01N 15/08; E21B 49/005; E21B 49/00; E21B 49/02; E21B 43/00
USPC .................................................. 324/376–378
See application file for complete search history.

(56) References Cited

U.S. PATENT DOCUMENTS

| 4,490,676 A | 12/1984 | Davis, Jr. et al. |
| 4,499,418 A | 2/1985 | Helms et al. |
(Continued)

FOREIGN PATENT DOCUMENTS

| CN | 86 100 707 A | 1/1987 |
| DE | 76 38 683 U1 | 6/1977 |
(Continued)

OTHER PUBLICATIONS

Alvarado, F.E.,et al., Visualization of three phases in porous media using micro computed tomography, paper SCA2003-21 presented at the International Symposium of Society of Core Analysts, Pau, France (Sep. 21-24, 2003).
(Continued)

*Primary Examiner* — Raul J Rios Russo
(74) *Attorney, Agent, or Firm* — Choate, Hall & Stewart LLP; Charles E. Lyon; Peter Flynn

(57) ABSTRACT

An example system includes resonators configured for spatial distribution across a dimension of a target, with the resonators each being configured to transmit signals into the target and to receive signals through the target; and a data processing system to generate, based on the signals transmitted and received, a saturation profile of the target.

22 Claims, 6 Drawing Sheets

(56) References Cited

U.S. PATENT DOCUMENTS

| | | | |
|---|---|---|---|
| 4,543,821 A | 10/1985 | Davis, Jr. | |
| 5,341,101 A | 8/1994 | Maerefat et al. | |
| 5,351,521 A | 10/1994 | Cracknell | |
| 5,389,883 A | 2/1995 | Harper | |
| 5,485,743 A | 1/1996 | Taherian et al. | |
| 5,493,226 A | 2/1996 | Honarpour et al. | |
| 8,640,529 B2 | 2/2014 | Sinha | |
| 9,335,273 B2 | 5/2016 | Botto et al. | |
| 9,650,891 B2 | 5/2017 | Reid et al. | |
| 9,804,105 B2 | 10/2017 | Karimi et al. | |
| 2003/0011386 A1* | 1/2003 | Xie | G01N 27/06 324/694 |
| 2012/0309306 A1* | 12/2012 | Kim | H04B 5/0031 455/41.1 |
| 2013/0033272 A1 | 2/2013 | Folgeroe et al. | |
| 2013/0058379 A1* | 3/2013 | Kim | H04B 5/0081 375/146 |
| 2014/0182737 A1 | 7/2014 | Jones et al. | |
| 2014/0252250 A1* | 9/2014 | Botto | G01R 33/0041 250/564 |
| 2014/0298900 A1* | 10/2014 | Clarke | E21B 49/00 73/152.55 |
| 2014/0323363 A1 | 10/2014 | Perriat et al. | |
| 2015/0042173 A1* | 2/2015 | Lee | H02J 5/005 307/104 |
| 2015/0212228 A1* | 7/2015 | Seleznev | G01N 33/241 702/7 |
| 2015/0376493 A1 | 12/2015 | Huh et al. | |
| 2016/0077022 A1 | 3/2016 | Waglohner et al. | |
| 2017/0059492 A1 | 3/2017 | Karimi et al. | |
| 2017/0248506 A1 | 8/2017 | Gupta et al. | |
| 2017/0350830 A1 | 12/2017 | Karimi et al. | |
| 2017/0361376 A1 | 12/2017 | Murugesan et al. | |
| 2018/0011033 A1 | 1/2018 | Karimi et al. | |
| 2019/0257771 A1* | 8/2019 | Desmulliez | H01Q 13/02 |

FOREIGN PATENT DOCUMENTS

| | | | |
|---|---|---|---|
| DE | 154 639 A1 | 4/1982 | |
| EP | 0 558 759 A1 | 9/1993 | |
| GB | 1 593 173 A | 7/1981 | |
| JP | S62169041 A | 7/1987 | |
| WO | WO-2017/040102 A1 | 3/2017 | |
| WO | WO-2019/166870 A1 | 9/2019 | |

OTHER PUBLICATIONS

Amyx, J.W. et al., Petroleum Reservoir Engineering, Physical Properties, McGraw Hill Book Co., New York, Indian Edition, 629 pages (1960).

Ayub, M. and Bentsen, R. G., An Apparatus for Simultaneous Measurement of Dynamic Saturation and Capillary Pressure Profiles, Paper 99-72: presented at the CSPG and Petroleum Society Joint Convention, Digging Deeper, Finding a Better Bottom Line, Calgary, Alberta, Canada, 13 pages (Jun. 14-18, 1999).

Ayub, M. and Bentsen, R. G., Measurement of Dynamic Saturation Profiles, Journal of Canadian Petroleum Technology, 39(9): 54-61 (2000).

Bail, P.T. and Marsden, S.S., Saturation distribution in a linear system during oil displacement, Producers Monthly, 21(8): 22-32 (1957).

Brost, D.F. and Davis, L.A., Determination of oil saturation distribution in field cores by microwave spectroscopy, SPE 10110, presented at the 56th Annual Fall Technical Conference and Exhibition, Society of Petroleum Engineers of AIME, San Antonio, TX, 19 pages (Oct. 5-7, 1981).

Caudle, B.H. et al., Further developments in the laboratory determination of relative permeabilities, Trans. AIME, 192: 145-150 (1951).

Chatenever, A. and Calhoun, J.C. Jr., Visual examinations of fluid behavior in porous media—Part 1, Trans. AIME, 195: 149-156 (1952).

Craig, F.F., Jr., The Reservoir Engineering Aspects of Waterflooding, Monograph vol. 3 of the Henry L. Doherty Series, Millet the Printer, Dallas, TX, 141 pages (1971).

Davis, L.A. Jr., Computer-controlled measurement of laboratory areal flood saturation distributions, SPE 12037, presented at the 58th Annual Fall Technical Conference and Exhibition, Society of Petroleum Engineers of AIME, San Francisco, CA, 8 pages (Oct. 5-8, 1983).

Davis, L.A. Jr., VHF electrical measurement of saturation in laboratory floods, Paper SPE No. 8847 presented at the First Joint SPE/DOE Symposium on Enhanced Oil Recovery, Tulsa, Oklahoma, 10 pages (Apr. 20-23, 1980).

Geffen, T.M. and Gladfelter, R.E., A note on the X-ray absorption method of determining fluid saturations in cores, Petroleum Transactions, AIME, 195: 322-323 (1952).

Honarpour, M. and Mahmood, S.M., Relative permeability measurements: An Overview, Journal of Petroleum Technology, SPE 18565: 963-966 (Aug. 1988).

Honarpour, M., et al., Relative Permeability of Petroleum Reservoir, CRC Press, Inc., Boca Raton, FL, USA, 154 pages (1986).

Kantzas, A., Investigation of physical properties of porous rocks and fluid flow phenomena in porous media using computer assisted tomography, In Situ, 14(1): 77-132 (1990).

Laird, A.D.K. and Putman, J.A., Fluid saturation in porous media by X-ray techniques, Petroleum Transactions, AIME, 192: 275-284 (1951).

Leverett, M.C. and Lewis, W.B., Steady flow of gas-oil-water mixtures through unconsolidated sands, Petroleum Transactions, AIME, 142: 107-116 (1941).

Parsons, R.W., Microwave Attenuation—A new tool for monitoring saturations in laboratory flooding experiments, Society of Petroleum Engineers Journal, 15(4): 302-310 (1975).

Stanley, M., Magnetometers come in multiple flavors, Me and My Smarter World, NXP, 4 pages (Mar. 4, 2011). URL: <https://blog.nxp.com/sensors/magnetometers-come-in-multiple-flavors>. [Retrieved Apr. 18, 2018].

Swanson, B.F., Visualizing Pores and Nonwetting Phase in Porous Rock, Journal of Petroleum Technology, 10-18 (1979).

Willhite, G.P., Waterflooding, Society of Petroleum Engineers, Richardson, TX., USA, SPE Textbook Series, vol. 3, 333 pages (1986).

Yadav, G.D. et al., Microscopic distribution of wetting and nonwetting phases in sandstones during immiscible displacements, SPE Reservoir Engineering, 2: 137-147 (1987).

International Search Report for PCT/IB2018/056518, 8 pages (dated Jan. 28, 2019).

Written Opinion for PCT/IB2018/056518, 9 pages (dated Jan. 28, 2019).

Invitation to Pay Additional Fees and Annex to Form PCT/ISA/206 Communication Related to the Search Results of the Partial International Search for PCT/IB2018/056518, 8 pages (dated Dec. 7, 2018).

Agar Corporation, OW-200 Series Oil/Water Meters Liquid/Liquid Concentration, Process Measurement & Control Solutions, 3 pages [Retrieved Online Jun. 19, 2018]. URL: http://www.agarcorp.com/literature/ow200.html.

Al-Taweel, A. B. and Barlow, S. G., Field Testing MultiPhase Meters, Society of Petroleum Engineers Inc. SPE 56583, 16 pages (1999).

Dongzhi, Z., Analysis of Multi-factor Influence on Measurement of Water Content in Crude Oil and Its Prediction Model, Proceedings of the 27th Chinese Control Conference, Kunming, Yunnan, China, 6 pages (Jul. 16-18, 2008).

Essiflo, Water Cut Meter, 5 pages [Retrieved Online Jun. 19, 2018]. URL: http://eesiflo.com/water-cut-meter.html.

Joshi, K.K. et al., Non-destructive Microstrip Resonator Technique for the measurement of moisture / permittivity in crude oil, Proceedings of the XXVIIIth URSI General Assembly, New Delhi, India, 8 pages (2005).

Karimi, M.A. et al., Design and Dynamic Characterization of an Orientation Insensitive Microwave Water-Cut Sensor, IEEE Transactions on Microwave Theory and Techniques, 66(1): 530-539 (2018).

(56) References Cited

OTHER PUBLICATIONS

Karimi, M.A. et al., Low Cost and Pipe Conformable Microwave-Based Water-Cut Sensor, IEEE Sensors Journal, 16(21): 7636-7645 (2016).
McKerricher, G. et al., Crude Oil Water-Cut Sensing with Disposable Laser Ablated and Inkjet Printed RF Microfluidics, IMS, 3 pages (2014).
Mohamed, A.-M. O. et al., Effect of salinity and temperature on water cut determination in oil reservoirs, Journal of Petroleum Science and Engineering, 40: 177-188 (2003).
Nyfors, E. G., Cylindrical Microwave Resonator Sensors for Measuring Materials Under Flow, Helsinki University of Technology, Report S243, 181 pages (May 2000).
Parker, A. and Joshi, S., M-Flow Technologies Ltd, 16040: Non-Intrusive Water Cut Measurement Based on a Composite Construction Material Platform, UPM Forum, Upstream Production Measurement, Houston, TX, 18 pages (Feb. 24-25, 2016).
Roxar, Roxar Watercut meter, Product Data Sheet, Emerson Process Management, 11 pages (Apr. 4, 2016). URL: http://www2.emersonprocess.com/siteadmincenter/PM%20Roxar%20Documents/Roxar%20Watercut%20meter%20Data%20Sheet.pdf.
Schematic drawing of core-flooding setup, ResearchGate, 4 pages [Retrieved Mar. 15, 2018]. URL: https://www.researchgate.net/figure/Schematic-drawing-of-core-flooding-setup-The-isolat...
Sun, X. et al., Application of Nanoparticles in Enhanced Oil Recovery: A Critical Review of Recent Progress, Energies, 10(345): 33 pages (2017).
Tosic, D. and Potrebic, M., Compact Multilayer Bandpass Filter with Modified Hairpin Resonators, Journal of Microelectronics, Electronic Components and Materials, 42(2): 123-130 (2012).
Weatherford International, Water-Cut Meters, 3 pages [Retrieved Online Jun. 19, 2018]. URL: https://www.weatherford.com/en/products-and-services/production/flow-measurement/water-cut-meters.
Wylie, S.R. et al., RF sensor for multiphase flow measurement through an oil pipeline, Meas. Sci. Technol., 17: 2141-2149 (2006).
Yang, Y.S. et al., The Design, Development and Field Testing of a Water-Cut Meter Based on a Microwave Technique, Society of Petroleum Engineers, SPE 20697: 775-782 (1990).
Written Opinion of the International Preliminary Examining Authority for PCT/IB2018/056518, 4 pages (dated Feb. 11, 2020).
International Preliminary Report on Patentability for PCT/IB2018/056518, 13 pages (dated Sep. 18, 2020).

* cited by examiner

DETECTING SATURATION LEVELS OF A SAMPLE CORE USING ELECTROMAGNETIC WAVES

TECHNICAL FIELD

This specification relates generally to example techniques for detecting saturation levels of a sample core using electromagnetic waves, such as microwaves.

BACKGROUND

A process known as waterflooding is used to displace, and to produce, hydrocarbons, such as oil or gas, from a reservoir when natural energy of the reservoir is insufficient to force the hydrocarbons toward and into a well, and then to the surface. Waterflooding may be performed in the field by pumping liquid, such as water, into a reservoir through one or more injection wells.

The resulting displacement of water for hydrocarbons caused by waterflooding may be modeled in a laboratory before actual field deployment. For this purpose, small pieces of rock, known as cores, are extracted from a rock formation in the reservoir. The cores are used to mimic the waterflooding process in the laboratory. Experiments performed in the laboratory, known as coreflooding, may be used to determine saturation profiles for the core and, thus, for the reservoir.

During coreflooding, fluid, such as water, is injected into a core saturated with oil extracted from the reservoir. Measurements are taken based on the fluid injection in order to estimate the performance of the reservoir when subjected to waterflooding. In some cases, waterflooding parameters may be adjusted based on measurements taken during the coreflooding process in order to affect hydrocarbon yield from the reservoir.

SUMMARY

An example system includes resonators configured for spatial distribution across a dimension of a target. The resonators are each configured to transmit signals into the target and to receive signals through the target. A data processing system is configured to generate, based on the signals transmitted and received, a saturation profile of the target. The example system may include one or more of the following features, either alone or in combination.

The data processing system may be configured to perform an analysis of the signals transmitted and received from each of the resonators and, based on the analysis, to determine a resonance frequency of each of the resonators. The data processing system may be configured to identify a resonance frequency of each of the resonators based on destructive interference resulting from transmitted and reflected signals. The data processing system may be configured to determine attenuation of the signals transmitted into the target. The saturation profile may be based on the attenuation of the signals in the target. The data processing system may be configured to determine, as part of the saturation profile, relative amounts of hydrocarbon and water in each segment of the target that is proximate to a corresponding resonator.

The saturation profile may identify relative amounts of hydrocarbon and water in segments that are spatially distributed across a dimension of the target. The saturation profile may include a temporal component and a spatial component. The temporal component may be indicative of a duration of at least part of the spatial component. The target may include a core of a reservoir formation comprised of porous rock, and the core may be held by a core holder. The resonators may be formed on the core holder.

The example system may include a microwave feeding structure having one or more common ports. Each of the resonators may include a port. The data processing system may be configured to access a resonator among the resonators through a port on the resonator and one of the common ports. The microwave feeding structure may be formed on the core holder. A switch may be configured to selectively connect a port of a resonator and a common port to the data processing system. The resonators may include microwave resonators, and the signals may include microwave signals.

Some implementations of the example systems may have one or more of the following advantages. The example systems may generate improved quality saturation data, leading to accurate permeability curves. The example systems may be able to obtain real time dynamic saturation profiles of two-phase—for example, oil and water—flow, while operating at reservoir conditions of temperature and pressure. The example systems may be used to obtain real-time dynamic saturation profiles during gas and water coreflood experiments at reservoir conditions of temperature and pressure. The example systems may have equal applicability to steady-state and to unsteady-state coreflood experiments. The example systems may be configured to determine saturation profiles for consolidated and unconsolidated porous media. Saturation profiles generated by the example systems may provide an indirect view of pore or grain distribution, or core heterogeneity, along the core. The dynamic saturation profiles generated by the example systems may be used to observe real-time flood-front movement, frontal stability, and viscous fingering.

Any two or more of the features described in this specification, including in this summary section, may be combined to form implementations not specifically described in this specification.

At least part of the processes, methods, systems, and techniques described in this specification may be controlled by executing, on one or more processing devices, instructions that are stored on one or more non-transitory machine-readable storage media. Examples of non-transitory machine-readable storage media include, but are not limited to, read-only memory, an optical disk drive, memory disk drive, and random access memory. At least part of the processes, methods, systems, and techniques described in this specification may be controlled using a computing system comprised of one or more processing devices and memory storing instructions that are executable by the one or more processing devices to perform various control operations.

The details of one or more implementations are set forth in the accompanying drawings and the description subsequently. Other features and advantages will be apparent from the description and drawings, and from the claims.

DESCRIPTION OF THE DRAWINGS

Like reference numerals in different figures indicate like elements.

DETAILED DESCRIPTION

Figure 1:
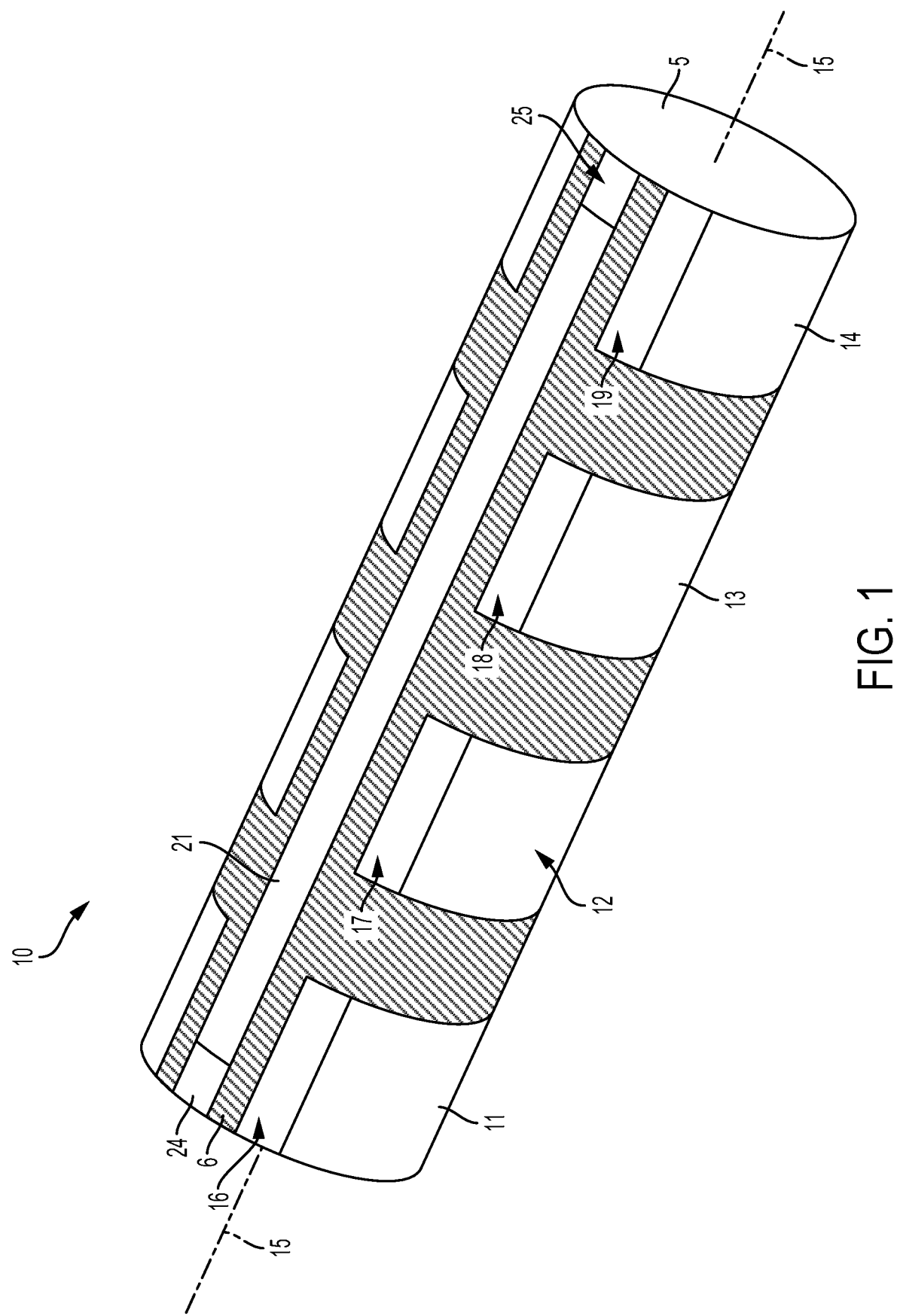
FIG. 1 is a perspective view of components of an example system installed around a sample core for detecting saturation levels of the core using microwaves.

Effective permeability is a relative measure of the conductance of a porous medium for one fluid phase when the medium is saturated with more than one fluid. Relative permeability (Kr) is the ratio of the effective permeability of a phase to a base permeability, for example, absolute permeability to air or water. Relative permeability is a parameter used for estimating performance of a hydrocarbon reservoir, such as an oil or petroleum reservoir. For example, relative permeability data may be used to simulate reservoir performance, to estimate past and present reservoir performance, and also to estimate future reservoir performance under operating conditions, such as varying temperature and pressure.

Relative permeability is a function of saturation, which is based on the relative amounts of water and hydrocarbon, such as gas or oil, present in a formation. Factors, such as rock and fluid properties of the formation, may also affect measurements of relative permeability. However, saturation levels typically have the greatest impact on shapes of relative permeability curves for the formation. In some cases, an error in the estimation of a saturation level can introduce an error into the formation's relative permeability data. This error can have a negative impact on reservoir performance simulation results.

Coreflooding experiments may be used to estimate the saturation level of formation, for example, to estimate the relative amounts of hydrocarbon and water in a core taken from the formation. Knowing the saturation level, it is possible to estimate the relative permeability of the formation from which the core was taken.

Described in this specification is an example system, and associated processes, that may be used during coreflooding experiments. In an implementation, the system includes one or more microwave resonators that are spatially-distributed along a longitudinal dimension of a sample core, or other appropriate target, and that are used to determine a ratio of hydrocarbon to water in individual longitudinal segments of the core. In some implementations, the system is configured to detect the resonance frequency of each microwave resonator and, based on the detected resonance frequency, to determine the relative amounts of hydrocarbon and water in a segment of the core proximate to that microwave resonator. In some implementations, the system is configured to detect attenuation of microwaves in the core. In some implementations, the system is configured to determine relative amounts of hydrocarbon and water in a segment of the core based on the attenuation detected.

In an example, water and hydrocarbon molecules are distinguishable based upon their different responses to external microwave fields. Water molecules can be distinguished from hydrocarbon molecules, such as oil molecules, which have smaller dipole moments than water. Having a large dipole moment, water molecules tend to respond more strongly than, and to offer more resistance than, oil molecules to signal propagation. In this regard, water has large relative electric permittivity of about eighty (80) compared to the relative electric permittivity of hydrocarbons, which may be between two (2) and two-and-a-half (2.5). Microwaves thus travel more slowly in water than in hydrocarbons, such as oil. Therefore, water can be distinguished from hydrocarbons based on the speed of travel of microwaves in both water and hydrocarbons. Attenuation of microwaves that results from transmission through the core is indicative the percentages of hydrocarbon and water in the core.

The contrast in dielectric properties between water and hydrocarbon, such as oil, can also be used to estimate the fractional distribution of water and hydrocarbon in coreflooding experiments. That is, as the water saturation in a porous medium, such as a core, increases, the dielectric constant of the core's matrix also increases, thereby decreasing the resonance frequency of the microwave resonator. In other words, one can estimate the water fraction in a core by measuring the resonance frequency of a microwave resonator proximate to the core. Relevant to this is that transmitted and reflected microwaves produce destructive interference at the resonance frequency. Accordingly, destructive interference of transmitted and reflected waves may be measured to identify the resonance frequency.

Parts of the system, such as the microwave resonators and associated components, may be incorporated into existing core holders. The microwave resonators and associated components may be formed on—for example, printed on— the exterior of a core holder and, as a result, may occupy little extra space. For example, printable conductive inks or pastes, such as ink jet or screen-printable materials, may be formed on a sleeve of the core holder. An example of such a material is a silver paste, which has a low conductor loss and can be printed on the core holder. However, the system is not limited to use with this material.

In this example, the system is completely noninvasive, is configured to estimate the saturation level of a core as explained, and is configured to obtain dynamic saturation profiles of the core as a function of time and distance along a core holder. This information may be used to estimate the relative permeability of the core and, thus, of the formation from which the core was extracted.

Figure 2:
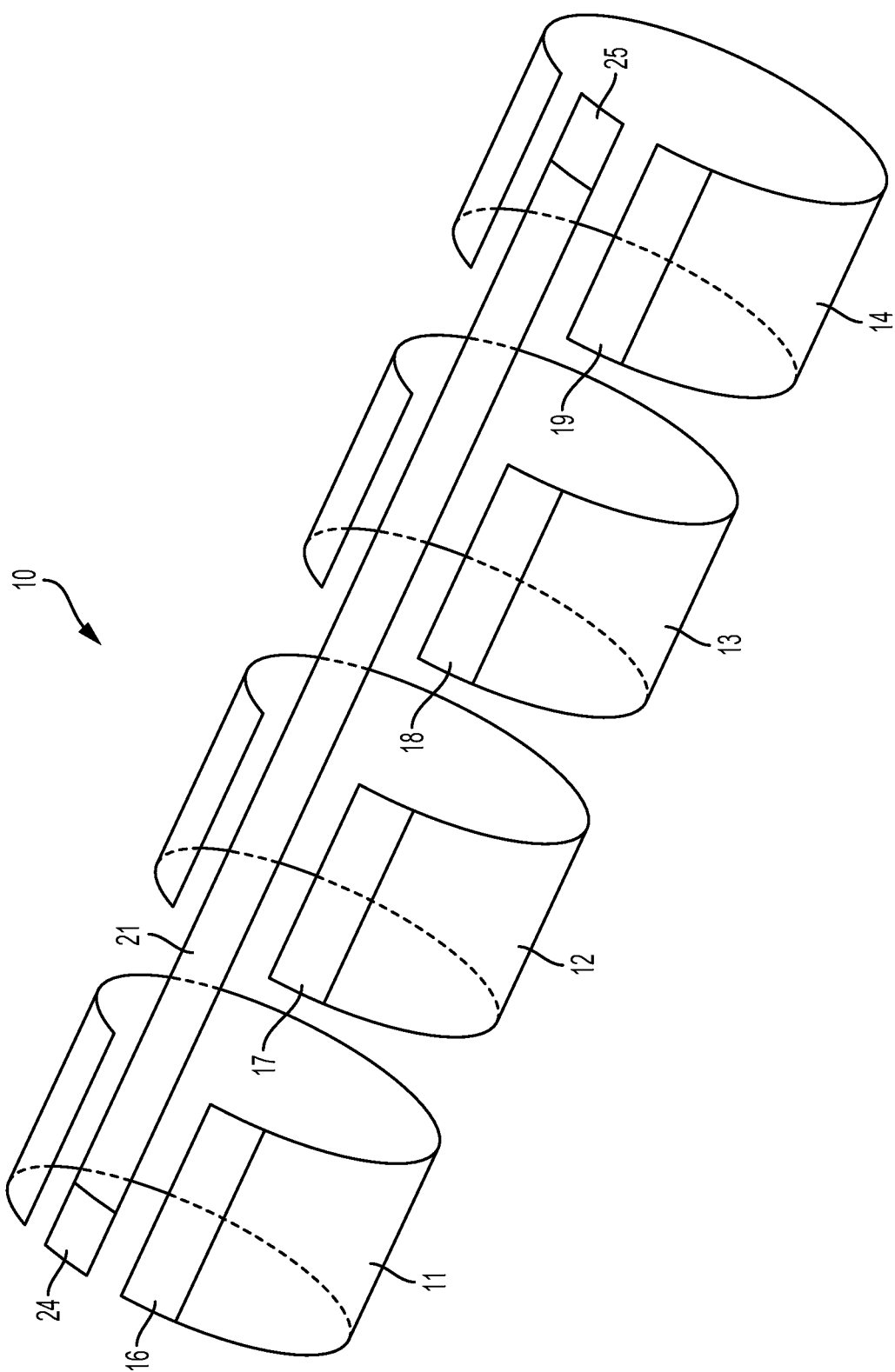
FIG. 2 is perspective view of the components of FIG. 1 absent the core.

FIGS. 1 and 2 show components 10 of an example system. In FIG. 1, components 10 are mounted on a core 5 and, in FIG. 2, components 10 are shown absent core 5 and core holder 6. Core 5 is held by a core holder 6 that, generally, conforms to the shape of the core.

In the example of FIGS. 1 and 2, components 10 includes four microwave resonators 11, 12, 13, 14. The system is not restricted to use of a specific type of resonator. Different types of resonators, such as a ring resonator and a T-resonator, may be used and configured for the system. Moreover, the system is also not limited to the number of microwave resonators used; any appropriate number of microwave resonators may be used depending upon the spatial resolution required or desired. As shown in FIG. 1, microwave resonators 11, 12, 13, 14 are spatially-distributed along a longitudinal dimension of core 5. The longitudinal dimension of core 5 is represented in FIG. 1 by dotted line 15. However, the system is not limited to this type of spatial distribution; any appropriate spatial distribution of microwave resonators may be used. Using spatially-distributed microwave resonators 11, 12, 13, 14, the saturation of individual core segments, each corresponding to, and proximate to, a microwave resonator, can be determined.

In some implementations, the microwave resonators each have a resonance frequency that is inversely proportional to the square root of the dielectric constant of the medium on which the resonators are installed, in this example, the core. Water distribution can be determined due to its greater dielectric constant compared to other mediums present inside the core, such as hydrocarbons and air. In a T-resonator; incident microwaves are superimposed onto reflected microwaves resulting in destructive interference at the resonance frequency. At this frequency, microwaves are not passed from one port of the resonator to the other. Since water has quite a large dielectric constant (about 80) compared to oil (about 2.2) and air (about 1); it is possible to distinguish these substances and their relative quantities by measuring the resonance frequency.

The system may be implemented using one of multiple example designs. In the first example design shown in FIGS. 1 and 2, a common feedline (for example, microwave feeding structure 21) capacitively couples all of the resonators. A transmission/reflection coefficient can be measured between a common feedline port and each respective resonator's port (references 16, 17, 18, 19 of FIG. 1). The common feedline, examples of which include a microstrip or co-planar wave guide (CPW), defines common feedline ports 24, 25, through which the microwave resonators are monitored. The individual microwave resonators may be coupled to the microwave feeding structure directly, capacitively, or through one or more other appropriate coupling mechanisms.

Figure 5:
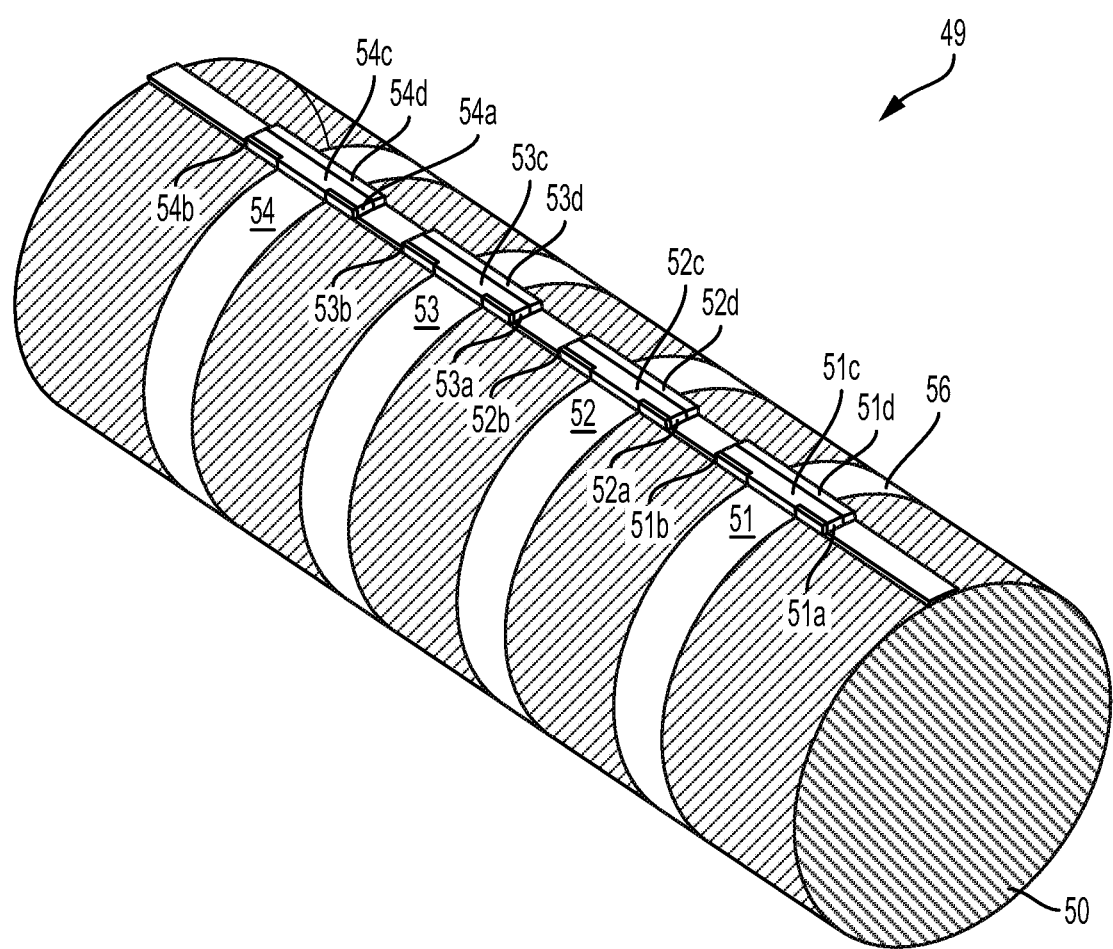
FIG. 5 is perspective view of components of another example system for detecting saturation levels of a sample core using microwaves.
Figure 6:
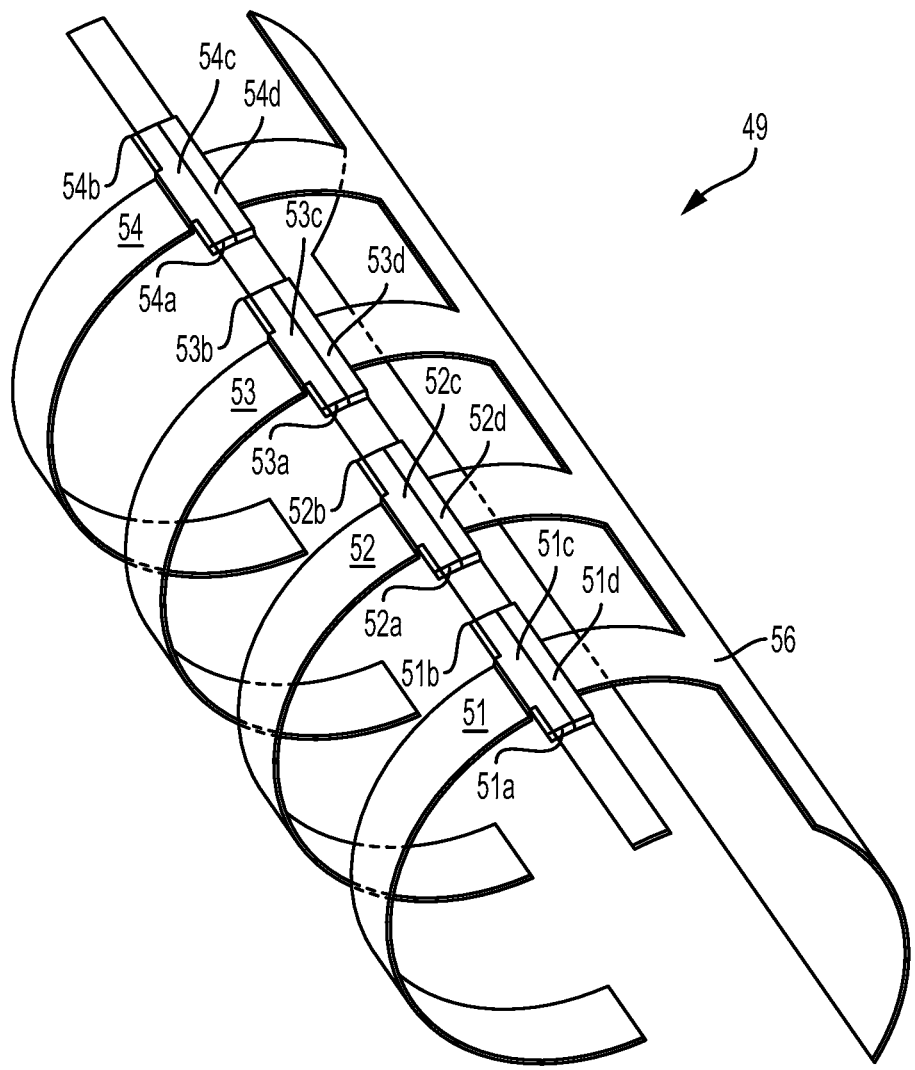
FIG. 6 is perspective view of the components of FIG. 5 absent the core.

In another example design 49 shown in FIGS. 5 and 6, each of the microwave resonators can be configured to transmit and to receive microwaves through core 50 (shown in FIG. 5 only). Core 50 may, or may not, disposed in a core holder. The resonance frequency of each resonator may be measured based on its transmission and reflection coefficients. As shown in FIGS. 5 and 6, each microwave resonator 51, 52, 53, 54 is a T-resonator having two ports —51a, 51b; 52a, 52b; 53a, 53b; 54a, 54b, respectively. In this example design, a common ground plane is divided into four branches, which are combined together to act as the common ground plane for the feedlines of four T-resonators. As shown in FIGS. 5 and 6, the feedline ground 56 is branched, and is common to each of the signal lines 51c, 52c, 53c, 54c. Feedline ground 56 is separated from each signal line by a corresponding dielectric separator 51d, 52d, 53d, 54d having a predefined width. In some examples, the dimensions of each signal line and the ground plane may be optimized to match the impedance to 50 ohms ($\Omega$). The feedline signal may be connected using a curved shaped conductor, which acts as a quarter-wavelength ($\lambda/4$) open stub at a certain microwave frequency. As noted and as shown in FIGS. 5 and 6, in this example design, each resonator has two ports—one port to transmit, and one port to receive, a microwave signal. As was the case in the example first design, the resonance frequency of each resonator can be determined based on its transmission/reflection coefficients.

The system may be configured to measure the resonance frequency of each of the microwave resonators, to measure the attenuation of microwaves transmitted through the core, or both. In some examples, each of the microwave resonators may be configured as a two-port resonator, with one port on the resonator itself and the other port on the microwave feeding structure 21 (FIG. 1). In an example, the resonance frequency of each resonator may be measured using a vector network analyzer (VNA) or other circuitry, such as a microwave oscillator, that is electrically connected to the microwave resonators via a switch. In this example, the VNA is configured to observe the band-pass or band-stop response of the microwave resonators.

Figure 3:
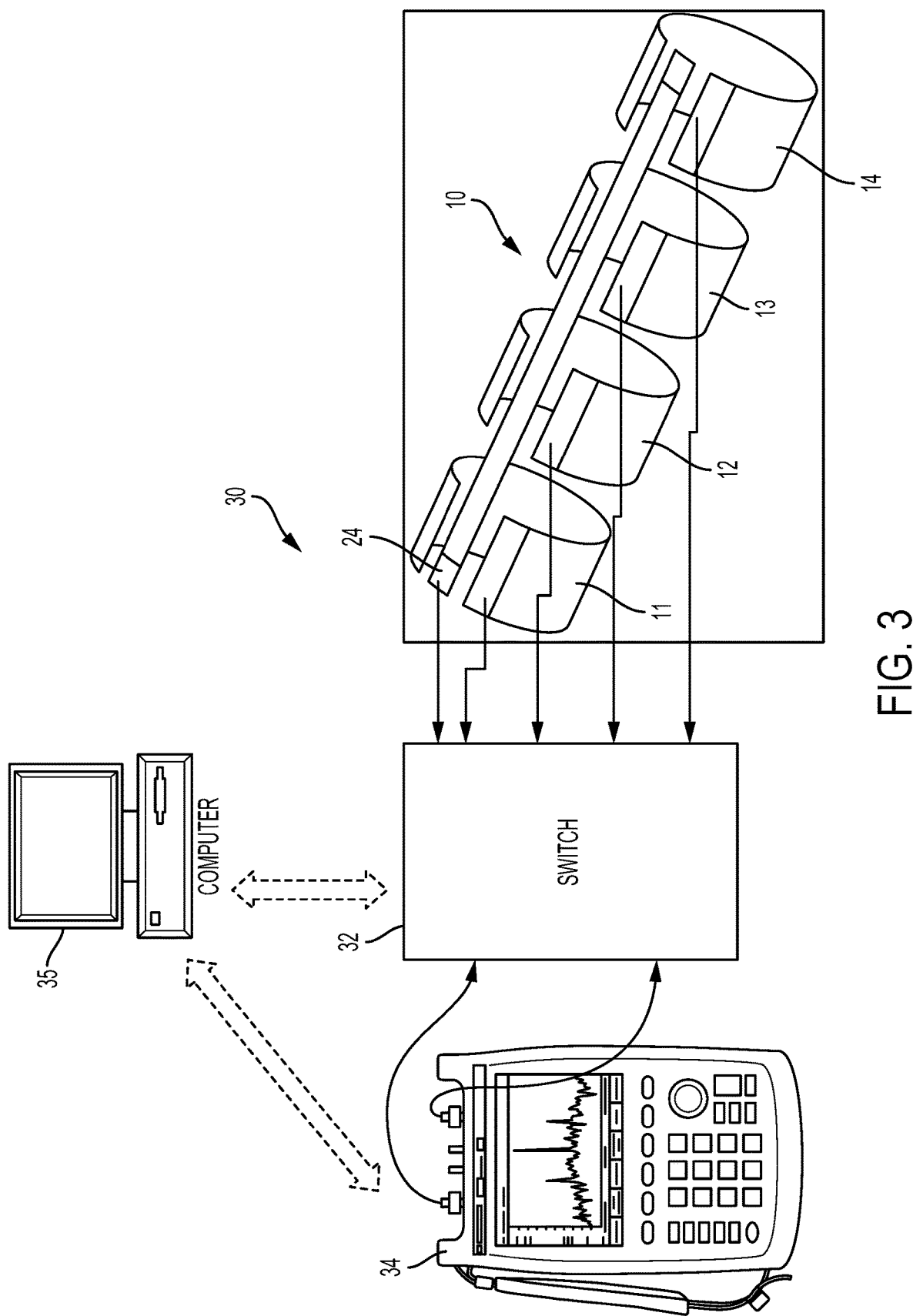
FIG. 3 is a block diagram of an example system containing the components of FIGS. 1 and 2.

FIG. 3 shows an example system 30 that includes components 10 of FIGS. 1 and 2. System 30 may include a switch 32 that is configured to connect, in turn, each of the microwave resonators 11, 12, 13, 14 to VNA 34. The switch may be controlled by a computing system, such computing system 35.

In this example, VNA 34 is configured to receive, via switch 32, signals from each of the microwave resonators. VNA 34 may be implemented as a stand-alone instrument, as shown, or as part of a data processing system. The data processing system may include computing system 35, examples of which are described in this specification. Computing system 35 may be configured to communicate with VNA 34 and switch 32, as represented by the dashed arrows.

The data processing system, including VNA 34, may be configured to capture raw microwave resonance data from the microwave resonators, to perform appropriate conversions on the data, and to process the data to produce saturation profiles for the core over time. For example, the data processing system may be configured to analyze the signals from each of the microwave resonators and, based on the analysis, to determine the resonance frequency of each of the microwave resonators. As explained previously, incident microwaves superimposed onto reflected microwaves cause destructive interference at the resonance frequency. At this frequency, microwaves are not passed from one port of the resonator to another port of the resonator. As a result, when a microwave resonator is operating, and low-level signals or undetectable signals are identified for that microwave resonator at VNA 34, the data processing system may determine that the frequency at which that microwave resonator is operating is the resonant frequency of that microwave resonator. An undetectable signal may be identified based on knowledge that the microwave resonator is operating and that a signal should be received as a result of the microwave resonator operating, but that the signal has not been received. Based on the detected resonance frequency, the system may determine the relative amounts of hydrocarbon and water in the segment of the core that is proximate to that microwave resonator.

The data processing system may be integrated into an existing data processing system that is used to acquire pressure and production data during a coreflooding experiment. The data recorded by the system may include, but is not limited to, data relating to pressure, total production, flowrate, and temperature associated with the coreflooding experiment.

The resonance frequency measurement obtained by the data processing system may be a real-time measurement. In this regard, in some implementations, real-time may not mean that two actions are simultaneous, but rather may include actions that occur on a continuous basis or track each other in time, taking into account delays associated with processing, data transmission, hardware, and the like. The resolution of the system may be dependent on a number of factors. Example factors are described in this specification. In some implementations, the system is configured to have a resolution of about one (1) inch or 2.54 centimeters (cm). In some implementations, having a longitudinal resolution of about one inch, the system may have a time resolution of about one (1) to five (5) second. The time component may be an indication of the duration over which the saturation represented by the spatial component occurred. However, the system is not limited to these values; the system may be configured to achieve any appropriate resolutions. Ideally, it is desired to know the amount and location of water in the core—referred to as geometric distribution of water inside the core—at as great a resolution as possible.

The example of FIG. 3 may include components of FIGS. 5 and 6 substituted for the components of FIGS. 1 and 2 shown in the figure.

Figure 4:
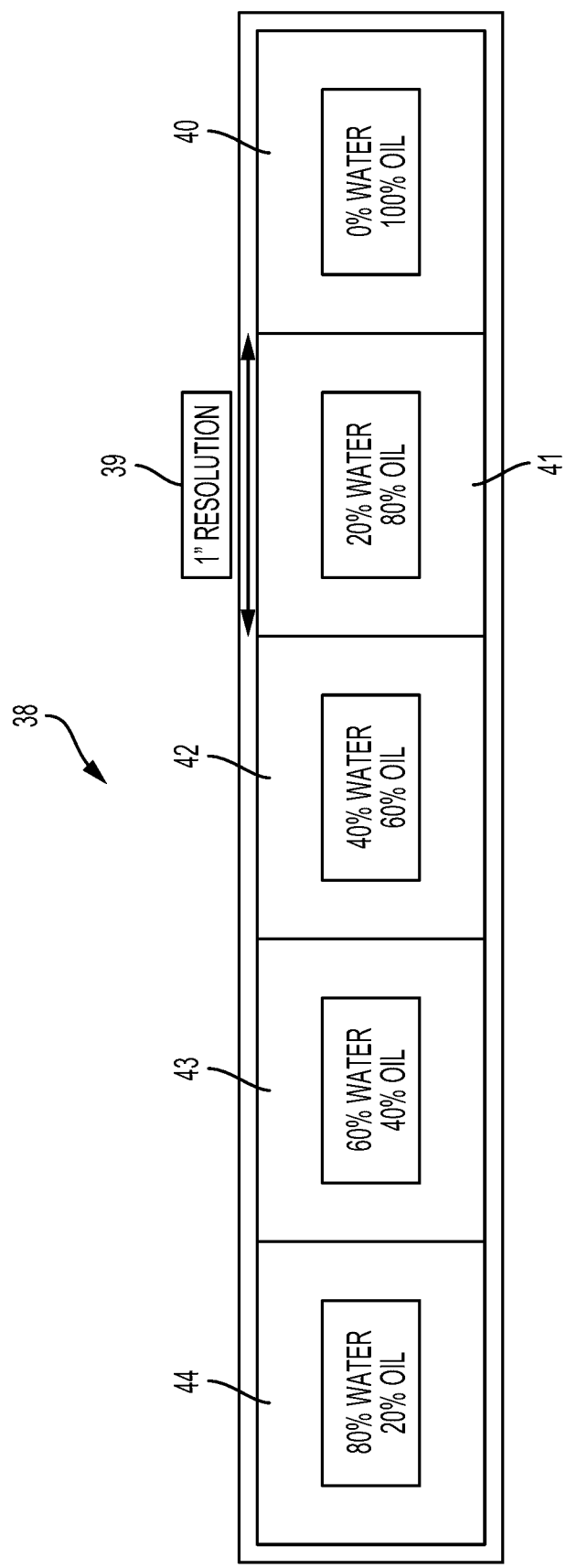
FIG. 4 is a cut-away view of an example core and saturation profiles for segments of the example core.

FIG. 4 shows an example of a core 38 that has been analyzed by a variant of system 30 at a one-inch spatial resolution. More specifically, in a core flooding experiment, the amount of water relative to hydrocarbon, such as oil, is determined for core 38. In this example, core 38 is analyzed by a system like system 30, except the system that performed the analysis has five (5) microwave resonators instead of four microwave resonators. In this example, analysis of the resonance frequency of the microwave resonators yields saturation information for each inch 39 (of a one-inch resolution system) of core 38, with each inch corresponding to the position of a microwave resonator. In this example, segment 40 contains 0% water and 100% oil; segment 41 contains 20% water and 80% oil; segment 42 contains 40% water and 60% oil; segment 43 contains 60% water and 40% oil; and segment 44 contains 80% water and 20% oil. Other examples may have different numbers of segments and different saturation information of water and hydrocarbon for each segment. In a core flooding experiment, a saturation profile may be obtained with respect to both distance and time. For example, saturation profiles may be obtained for the spatial extent of the core and during the time that fluid is added to the core.

An example factor in determining a frequency range of the microwave resonators is the diameter of the core, such as core 5 or 38. For instance, a core diameter of one (1) inch may result in a resonance frequency in the range of 0.5 GHz (gigahertz) to 5 GHz depending upon the shape and placement of the resonators and the locations and amounts of liquid inside the core. Multiple microwave resonators of the type noted may be useful in achieving greater longitudinal resolution while determining a geometric distribution of water inside the core sample.

In some implementations, the example system is configured to determine two-phase—for example, oil-water or gas-water—flow saturation profiles for time and distance along the core holder. In some implementations, the microwave resonators may be configured to use specific ranges for microwave frequency and power. For example, in some implementations, power levels of the microwave resonators can be as small as −10 dBm (decibel, referenced to milliwatts) (0.1 mW-milliwatts) to 0 dBm (1 mW) and frequency, as stated previously, may be in the range of 0.5 GHz to 5 GHz. However, the example system is not limited to use with these values; any appropriate power levels and frequencies may be used.

The relationship between resonance frequency and water content may not be linear because of the complex nature of the interaction among electromagnetic waves, hydrocarbon, and the core. Generally, the dielectric behavior of heterogeneous mixtures such as a water-oil in a porous medium has a complicated dependence on frequency and the matrix. Therefore, in some implementations, in order to determine the saturation profiles of a core, a system may determine any complex behavior empirically. The complex behavior may be used to establish, beforehand, a proper measurement method or workflow.

As noted, the example system may be used with existing core holders used in coreflooding experiments. Alternatively, in some examples, a high-pressure high-temperature (HPHT), core holder may be constructed from a different material, such as polyether ether ketone (PEEK), that does not interfere with microwaves. The microwave resonators and appropriate associated circuitry may be made small enough to be installed close to the core. Such an installation may reduce possible artifacts that may provide erroneous data resulting from an adjacent core holder rubber sleeve and confining liquid. Also, such a system reduces the need of any bulky hardware to characterize the core sample during the core flooding experiment, making the system compact. The system may be configured to withstand operational temperature and pressure conditions encountered in reservoirs. In some examples, the system may be configured to operate in reservoir temperatures that range from 80° C. (Celsius) to 150° C. and reservoir pressures that range from 2000 psi (pounds-per-square-inch) to 8000 psi; however, the system is not limited to use with reservoirs having these temperature and pressure characteristics.

The example system described in this specification may be implemented for wells that are vertical or for wells that are, in whole or part, non-vertical. For example, the system may be used to analyze cores of vertical well, a deviated well, a horizontal well, or a partially horizontal well, where horizontal is measured relative to the Earth's surface in some examples.

The example system described in this specification employs microwave resonators. However, the system is not limited to use with microwaves. Any appropriate electromagnetic waves and electromagnetic wave resonators may be used in place of the microwave resonators. For example, radio frequencies and radio frequency resonators may be used instead of microwave frequencies and microwave frequency resonators. In an example, radio frequencies extend from 3 Hertz (Hz) to 300 GigaHertz (Ghz). In an example, microwave frequencies extend from 0.3 GHz to 300 GHz.

All or part of the system and processes described in this specification and their various modifications (subsequently referred to as "the processes") may be controlled at least in part, by one or more computers using one or more computer programs tangibly embodied in one or more information carriers, such as in one or more non-transitory machine-readable storage media. A computer program can be written in any form of programming language, including compiled or interpreted languages, and it can be deployed in any form, including as a stand-alone program or as a module, part, subroutine, or other unit suitable for use in a computing environment. A computer program can be deployed to be executed on one computer or on multiple computers at one site or distributed across multiple sites and interconnected by a network.

Actions associated with controlling the processes can be performed by one or more programmable processors executing one or more computer programs to control all or some of the operations described previously. All or part of the processes can be controlled by special purpose logic circuitry, such as, an FPGA (field programmable gate array), an ASIC (application-specific integrated circuit), or both an FPGA and an ASIC.

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, such as magnetic, magneto-optical disks, or optical disks. Non-transitory machine-readable storage media suitable for embodying computer program instructions and data include all forms of non-volatile storage area, including by way of example, semiconductor storage area devices, such as EPROM (erasable programmable read-only memory), EEPROM (electrically erasable programmable read-only memory), and flash storage area devices; magnetic disks, such as internal hard disks or removable disks; magneto-optical disks; and CD-ROM (compact disc read-only memory) and DVD-ROM (digital versatile disc read-only memory).

Elements of different implementations described may be combined to form other implementations not specifically set forth previously. Elements may be left out of the processes described without adversely affecting their operation or the operation of the system in general. Furthermore, various separate elements may be combined into one or more individual elements to perform the functions described in this specification.

Other implementations not specifically described in this specification are also within the scope of the following claims.

What is claimed is:

1. A system comprising:
   resonators configured for spatial distribution across a dimension of a target, the resonators each being configured to transmit signals into the target and to receive signals through the target; and
   a data processing system to generate, based on the signals transmitted and received, a saturation profile of the target.

2. The system of claim 1, where the data processing system is configured to perform an analysis of the signals transmitted and received from each of the resonators and, based on the analysis, to determine a resonance frequency of each of the resonators.

3. The system of claim 2, where the data processing system is configured to identify a resonance frequency of each of the resonators based on destructive interference resulting from transmitted and reflected signals.

4. The system of claim 1, where the data processing system is configured to determine attenuation of the signals transmitted into the target, the saturation profile being based on the attenuation of the signals in the target.

5. The system of claim 1, where the data processing system is configured to determine, as part of the saturation profile, relative amounts of hydrocarbon and water in each segment of the target that is proximate to a corresponding resonator.

6. The system of claim 1, where the saturation profile identifies relative amounts of hydrocarbon and water in segments that are spatially distributed across a dimension of the target.

7. The system of claim 1, where the saturation profile comprises a temporal component and a spatial component, the temporal component being indicative of a duration of at least part of the spatial component.

8. The system of claim 1, where the target is a core of a reservoir formation comprised of porous rock, the core being held by a core holder; and
   where the resonators are formed on the core holder.

9. The system of claim 8, further comprising:
   a microwave feeding structure comprising at least one common feedline capacitively coupling the resonators, the at least one common feedline comprising one or more common ports;
   where each of the resonators comprises a port; and
   where the data processing system is configured to access a resonator among the resonators through a port on the resonator and one of the common ports.

10. The system of claim 9, where the microwave feeding structure is formed on the core holder.

11. The system of claim 9, further comprising:
    a switch to selectively connect a port of a resonator and a common port to the data processing system.

12. The system of claim 1, where the resonators comprise microwave resonators, and the signals comprise microwave signals.

13. The system of claim 1, further comprising:
    at least one common feedline capacitively coupling the plurality of resonators, the at least one common feedline comprising one or more common ports;
    where each of the resonators comprises a port; and
    where the data processing system is configured to access each resonator among the resonators through a port on the resonator and one of the common ports.

14. The system of claim 1, comprising at least one common feedline capacitively coupling the resonators, where the at least one common feedline comprises at least one of a microstrip and a co-planar wave guide (CPW) through which the resonators are monitored.

15. The system of claim 1, further comprising a one-inch spatial resolution, where each inch of the one-inch spatial resolution corresponds to a position of a resonator of the plurality of resonators.

16. A method of generating a saturation profile of a target using resonators spatially distributed across a dimension of the target, the method comprising:
    capacitively coupling the resonators via a common feedline;
    transmitting signals into the target from the resonators;
    receiving signals through the target at the resonators; and
    generating a saturation profile of the target using a data processing system, the data processing system generating the saturation profile based on the signals transmitted and received,
    where the common feedline comprises one or more common ports;
    where each of the resonators comprises a resonator port; and
    where the data processing system is configured to access each resonator among the resonators through one of the common ports and one of the resonator ports.

17. The method of claim 16, where the data processing system performs an analysis of the signals transmitted and received from each of the resonators and, based on the analysis, determines a resonance frequency of each of the resonators.

18. The method of claim 17, where the data processing system identifies a resonance frequency of each of the resonators based on destructive interference resulting from transmitted and reflected ones of the signals.

19. The method of claim 16, where the target is a core of a reservoir formation comprised of porous rock, the core being held by a core holder; and
    where the resonators are formed on the core holder.

20. The method of claim 18, where each resonator comprises a port; and
    where the method further comprises selectively connecting a port of a resonator to the data processing system.

21. The method of claim 16, where the resonators comprise microwave resonators, and the signals comprise microwave signals.

22. A system comprising:
- a core holder conforming to a shape of a core, the core comprising a sample of a formation;
- a plurality of resonators spatially distributed across a dimension of the core holder, the plurality of resonators being formed on the core holder, each resonator of the plurality of resonators comprising:
  - a first port for transmitting at least one signal into the core;
  - a second port for receiving the at least one signal from the core;
  - a signal line; and
  - a dielectric separator;
- a feedline ground common to each signal line, the feedline ground being separated from each signal line by the corresponding dielectric separator; and
- a data processing system to generate, based on the signals transmitted and received, a saturation profile of the core.

* * * * *